(12) United States Patent
O'Lenick, Jr. et al.

(10) Patent No.: US 6,797,836 B1
(45) Date of Patent: Sep. 28, 2004

(54) RASPBERRY ALKOXY ESTERS AS A DELIVERY SYSTEM FOR NATURAL ANTIOXIDANTS

(75) Inventors: Anthony J. O'Lenick, Jr., Dacula, GA (US); Carter LaVay, Riverside, CT (US)

(73) Assignee: Zenitech LLC, Old Greenwich, CT (US)

( * ) Notice: Subject to any disclaimer, the term of this patent is extended or adjusted under 35 U.S.C. 154(b) by 0 days.

(21) Appl. No.: 10/601,618

(22) Filed: Jun. 24, 2003

(51) Int. Cl.$^7$ ................................................ C07C 57/00
(52) U.S. Cl. ..................... 554/224; 554/223; 424/732; 426/629
(58) Field of Search ....................... 554/223; 424/732; 426/629

(56) References Cited

U.S. PATENT DOCUMENTS 6,391,345 B1 * 5/2002 Heeg

* cited by examiner

Primary Examiner—Deborah D Carr

(57) ABSTRACT

The present invention relates to raspberry seed oil derivatives derived by the reaction of polyoxyalkylene glycol compounds and cold pressed raspberry seed oil. The choice of pressed raspberry seed oil as a raw material in the preparation of the compounds of the invention is critical, since it has been found that the cold pressed raspberry seed oil contains antioxidants, antimicrobial compounds and which when reacted with a polyoxyalkylene glycol compounds, result in products that deliver said actives to the skin and hair, resulting in protection of the skin and hair from environmental factors such as acid rain, ozone attack and UV degradation.

9 Claims, No Drawings

RASPBERRY ALKOXY ESTERS AS A DELIVERY SYSTEM FOR NATURAL ANTIOXIDANTS

BACKGROUND OF THE INVENTION

The present invention relates to raspberry seed oil derivatives derived by the reaction of polyoxyalkylene glycol and cold pressed raspberry seed oil. The choice of cold pressed raspberry seed oil as a raw material in the preparation of the compounds of the present invention is critical, since it has been found that the cold pressed raspberry seed oil contains a unique antioxidant which when reacted with polyoxyalkylene glycol resulting in products that deliver said actives to the skin and hair, resulting in protection of the skin and hair from environmental factors such as acid rain, ozone attack and UV degradation.

U.S. Pat. No. 6,391,345 issued May 2002 describes the refining of cold pressed cranberry seed oil, and is incorporated herein by reference. American cranberries, *Vaccinium macrocarpon*, are native plants of open, acid peat bogs in North America. Raspberry plants are evergreen perennial vines that produce runners and upright branches with terminal flower buds. This process is also applicable to raspberry seed oil.

Raspberries have historically been harvested and either ingested as whole berries, such as in raspberry sauce, or have been processed for their juice. Pulp remaining after raspberry juice extraction processing has historically been regarded as an undesirable waste product with little or no utility.

Raspberries are grown all over the world. They are a popular food, consumed in large quantities.

Raspberries contain ellagic acid ($C_{14}H_6O_8$). This acid is a non-flavonoid polyphenol present in the form of hydrolysable tannins, which has been found to protect chromosomes from radiation induced lipid peroxidation.

Raspberry oil contains a high level of omega 3 and omega 6 linoleic acid. These are essential fatty acids. Under normal circumstances, oils useful in the cosmetic industry are refined with a variety of steps that are designed to maximize triglyceride content, and minimize color and odor. These steps include steam distillation, a process in which steam is sparged through the oil to remove odor and color bodies and solvent extraction with compounds like hexane, which remove additional odor and color bodies. We have learned that these processes, while improving color and odor, remove many of the desirable "active" materials. What results is a light color, low odor triglyceride with no appreciable added skin benefits. We have surprisingly learned that when the raspberry seed oil that is cold processed is reacted with polyoxyalkylene glycol the actives (normally removed in non-cold press process) remain in the product, become water-soluble and have outstanding activity on the skin. In essence two things happen when the cold pressed raspberry seed oil is reacted with polyoxyalkylene glycol. First the triglyceride reacts polyoxyalkylene compound, giving a product that is water-soluble. Secondly, these specific compound solubilizes the active components there as a consequence of cold pressing. Thirdly, these very desirable materials are deposited on the skin by the ester, based upon its proclivity to remain on the skin. The result is a unique delivery of the actives to the skin from totally natural fruit oil.

The compounds of the present invention all get their unique properties in personal care applications from the cold pressed raspberry oil which is made water soluble by reaction with polyoxyalkylene glycol compounds.

SUMMARY OF THE INVENTION

The present invention relates to a series of products derived from the reaction of cold pressed raspberry oil and various polyoxyalkylene glycol compounds.

The present invention also relates to a process of treating hair and skin, which comprises contacting the hair and skin with an effective anti-oxidant containing amount of raspberry compounds of the preset invention.

DETAILED DESCRIPTION OF THE INVENTION

U.S. Pat. No. 6,391,345 issued May 2002 describes a cold pressed process for cranberry oil. We have surprisingly found that if the same process is used on raspberry oil specific antioxidant materials that are removed by more aggressive refining processes like solvent extraction. These compounds surprisingly survive the reaction with polyoxyalkylene glycol compounds, resulting in a highly substantive delivery system for these very desirable natural compounds.

Also critical to the practice of the present invention is the fatty composition of the cold pressed raspberry oil. This raspberry oil has a substantially clear appearance with a pale yellow color.

Cold Pressed Raspberry Oil is a triglyceride conforming to the following structure:

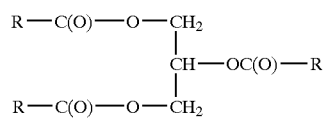

The oil is referred to as Rubus idaeus seed oil and has a CAS number of 381718-28-1

The R—C(O)— group has the following composition:

| Component | % Weight |
|---|---|
| 18:1 oleic | 10–20 |
| 18:2 linoleic | 30–40 |
| 18:3 linolenic (alpha) | 45–55 |
| alpha tocopherol | 46 mg/gram |
| Ellagic Acid | 450–650 ppm |

Distribution by type of fatty group

| Component | % Weight |
|---|---|
| Saturated | 3% |
| Polyunsaturated content | 86% |
| Mono unsaturated | 11% |

The oil contains the following very critical "active" components for skin and hair care:

| Material | Concentration |
|---|---|
| 18:3 linolenic (alpha) | 45–55% |
| alpha tocopherol | 46 mg/gram |
| Ellagic Acid | 450–650 ppm |

As can be seen, the cold pressed raspberry seed oil is a rich source of compounds having important properties when applied to hair and skin. The cold pressed raspberry oil can shield against UV-A induced damage by scattering light as well as by light spectrum absorption. The cold pressed raspberry oil has, then activity as a broad spectrum UV protectant. The raspberry oil may be used alone or in combination with other conventional sunscreens.

The ability to make derivatives of the oil in which the protection of the components of the cold pressed oil remain functional is a major aspect of the present invention.

Cold pressed raspberry seed oil has a very high concentration of gamma tocopherol. This level is much higher than is found in oils such as safflower and grape, which are 11 and 33, respectively. The gamma tocopherol has the most anti-oxidant capacity of all of the tocopherols and contributes to the stability of highly unsaturated oils in the raspberry oil. It is believed that the presence of the high gamma tocopherol concentration makes raspberry oil an excellent additive to animal food—both human and non-human. The gamma tocopherol may be as important as alpha tocopherol in preventing degenerative diseases.

Cold pressed raspberry seed oil has a high linolenic acid content. Linolenic acid has been implicated as a food additive and nutraceutical in preventing coronary heart disease and cancer. Raspberry oil also has a high polyunsaturated:saturated ratio in a neutral lipid fraction, of 10:1. This ratio is regarded as having value in reducing serum cholesterol, atherosclerosis and in preventing heart disease.

Cold pressed raspberry seed oil has a rather dark yellow to orange color because it contains carotenoids. The carotenoids are usable as colorant substitutes for materials such as carotenes, annotos, and apocarotenals used in the nutraceutical and oil industries.

The cold pressed raspberry seed oil, containing all of the above desirable compounds, is reacted with a polyoxyalkylene glycol conforming to the following structure:

$$HO-(CH_2-CH_2O)_a-(CH_2-CH_2(CH_3)O)_b-)CH_2-CH_2O)_cH$$

wherein
   a, b and c are independently integers ranging from 0 to 40, with the proviso that a+b+c equal at least 5.

To provide a composition conforming to the following structure:

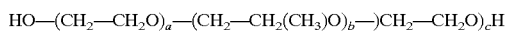

and

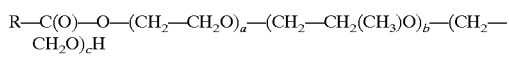

wherein;
   R is derived from cold pressed raspberry seed oil and has the composition;

| Component | % weight |
|---|---|
| 18:1 oleic | 10–20 |
| 18:2 linoleic | 30–40 |
| 18:3 linolenic (alpha) | 45–55 |
| alpha tocopherol | 46 mg/gram |
| Ellagic Acid | 450–650 ppm | and
   a, b and c are independently integers ranging from 0 to 40, with the proviso that a+b+c equal at least 5.

The reaction is a mixture of mono and di ester and is a consequence of the reaction process. Using an excess of raspberry oil results in more di-ester, but also results in a water insoluble oil that comes out of aqueous system.

The current invention describes a composition, which is prepared by the reaction of:
(1) cold pressed raspberry seed oil and
(2) polyoxyalkylene glycol confirming to the following structure;

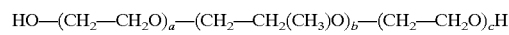

wherein
   a, b and c are independently integers ranging from 0 to 40, with the proviso that a+b+c equal at least 5.

The compounds of the present invention deliver these active products to skin, therefore the invention also discloses a process for conditioning skin which comprises contacting the skin with an effective conditioning concentration of a raspberry polyoxyalkylene ester composition, which conforms to the following structure;

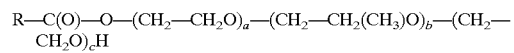

and

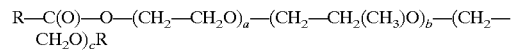

wherein;
   R is derived from cold pressed raspberry seed oil and has the composition;

| Component | % weight |
|---|---|
| 18:1 oleic | 10–20 |
| 18:2 linoleic | 30–40 |
| 18:3 linolenic (alpha) | 45–55 |
| alpha tocopherol | 46 mg/gram |
| Ellagic Acid | 450–650 ppm | and
   a, b and c are independently integers ranging from 0 to 40, with the proviso that a+b+c equal at least 5.

Preferred embodiments
In a preferred embodiment a is 5, b is 0, and c is 0.
In a preferred embodiment a is 5, b is 5, and c is 5.
In a preferred embodiment a is 0, b is 10, and c is 0.
In a preferred embodiment a is 10, b is 10, and c is 0.
In a preferred embodiment a is 20, b is 5, and c is 20.
In a preferred embodiment a is 1, b is 10, and c is 5.
In a preferred embodiment a is 40, b is 40, and c is 40.
In a preferred embodiment a is 10, b is 10, and c is 15.

EXAMPLES

The compounds of the present invention are made from commercially available raw materials.

Raw Materials

Cold Pressed Raspberry Seed Oil

Cold Presses Raspberry seed oil is an item of commerce sold by Regal Trade & Consult LLC. of Hoboken, N.J. It is processed using U.S. Pat. No. 6,391,345 issued May 2002, only applied to raspberry seed oil not cranberry seed oil.

Polyoxyalkylene Glycol

Polyoxyalkylene glycol compounds are items of commerce and arte available from a variety of sources including Siltech Corporation Toronto Ontario Canada. The structures presented were determined by NMR and are not dependant upon trade names.

| Example | a | b | c |
|---|---|---|---|
| 1 | 5 | 0 | 0 |
| 2 | 5 | 5 | 5 |
| 3 | 0 | 10 | 0 |
| 4 | 10 | 10 | 0 |
| 5 | 20 | 5 | 20 |
| 6 | 1 | 10 | 5 |
| 7 | 40 | 40 | 40 |
| 8 | 10 | 10 | 15 |

General Procedure

To grams of 400 grams of Cold Pressed Raspberry seed oil is added. The specified number of grams of polyoxyalkylene glycol (example 1–8). The reaction mass is heated to 180–200° C., under good agitation. As the reaction mass is held at temperature, the material clears and becomes homogeneous. The reaction mass is held for eight hours to 12 hours at reaction temperature. The reaction progress if followed by hydroxyl value and % ester. The resulting product is used without additional purification.

Polyoxyalkylene Glycol

| Example | Example | Grams |
|---|---|---|
| 9 | 1 | 111.0 |
| 10 | 2 | 368.5 |
| 11 | 3 | 296.0 |
| 12 | 4 | 516.0 |
| 13 | 5 | 1030.0 |
| 14 | 6 | 428.0 |
| 15 | 7 | 2806.0 |
| 16 | 8 | 846.0 |
| 17 | 1 | 222.0 |
| 18 | 2 | 737.0 |
| 19 | 3 | 592.0 |
| 20 | 4 | 1032.0 |
| 21 | 5 | 2059.0 |
| 22 | 6 | 856.0 |
| 23 | 7 | 5612.0 |
| 24 | 8 | 1692.0 |

Applications Examples

The compound of the present invention are water-soluble or water dispersible surface active compound that has an extraordinary skin feel and provide antioxidant, and other desirable properties from the components that are not removed from the raspberry oil when it is cold processed. The cold processing leaves behind the desirable components, which in turn are not destroyed by the reaction and surprisingly, become oil-soluble and delivered to the skin. In addition, materials are emulsifiers, and can be blended with dimethicone copolyol compounds to improve deposition on the skin.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A raspberry polyoxyalkylene glycol ester composition conforming to the following structure:

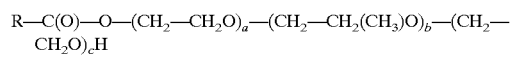

and

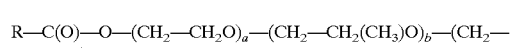

wherein;

R is derived from cold pressed raspberry;

a, b and c are independently integers ranging from 0 to 40, with the proviso that a+b+c equal at least 5.

2. A composition of claim 1 wherein a is 5, b is 0, and c is 0.

3. A composition of claim 1 wherein a is 5, b is 5, and c is 5.

4. A composition of claim 1 wherein a is 0, b is 10, and c is 0.

5. A composition of claim 1 wherein a is 10, b is 10, and c is 0.

6. A composition of claim 1 wherein a is 20, b is 5, and c is 20.

7. A composition of claim 1 wherein a is 1, b is 10, and c is 5.

8. A composition of claim 1 wherein a is 40, b is 40, and c is 40.

9. A composition of claim 1 wherein a is 10, b is 10, and c is 15.

* * * * *